United States Patent
Wu et al.

(10) Patent No.: US 12,059,436 B2
(45) Date of Patent: Aug. 13, 2024

(54) BCMA-CAR-T CELLS

(71) Applicants: ProMab Biotechnologies, Inc., Richmond, CA (US); Forevertek Biotechnology Co., Ltd, Changsha (CN)

(72) Inventors: Lijun Wu, Albany, CA (US); Vita Golubovskaya, Richmond, CA (US)

(73) Assignees: ProMab Biotechnologies, Inc., Richmond, CA (US); Forevertek Biotechnology Co., Ltd, Changsha (CN)

( * ) Notice: Subject to any disclaimer, the term of this patent is extended or adjusted under 35 U.S.C. 154(b) by 987 days.

(21) Appl. No.: 17/060,762

(22) Filed: Oct. 1, 2020

(65) Prior Publication Data
US 2021/0015870 A1  Jan. 21, 2021

Related U.S. Application Data

(63) Continuation of application No. PCT/US2019/023884, filed on Mar. 25, 2019.

(60) Provisional application No. 62/652,202, filed on Apr. 3, 2018.

(51) Int. Cl.
| | |
|---|---|
| *C07K 16/00* | (2006.01) |
| *A61K 35/17* | (2015.01) |
| *A61K 47/65* | (2017.01) |
| *C07K 14/705* | (2006.01) |
| *C07K 14/725* | (2006.01) |

(52) U.S. Cl.
CPC ............ *A61K 35/17* (2013.01); *A61K 47/65* (2017.08); *C07K 14/7051* (2013.01); *C07K 14/70521* (2013.01); *C07K 14/70578* (2013.01); *C07K 2317/56* (2013.01); *C07K 2317/622* (2013.01)

(58) Field of Classification Search
CPC .......... A61K 47/65; A61K 2239/38; A61K 39/4611; A61K 39/4631; C07K 14/7051; C07K 14/70521; C07K 14/70578; C07K 2317/56; C07K 2317/622
See application file for complete search history.

(56) References Cited

U.S. PATENT DOCUMENTS

2014/0363455 A1  12/2014  Stull et al.

FOREIGN PATENT DOCUMENTS

| WO | 2017211900 A1 | 12/2017 |
| WO | 2017218707 A2 | 12/2017 |

OTHER PUBLICATIONS

International Search Report dated Jun. 21, 2019 cited in PCT/US19/23884.
Marcela V. Maus, et al., "Antibody-modified T cells: CARs take the front seat for hematologic malignancies", Blood, Apr. 24, 2014, vol. 123, No. 17, pp. 2625-2635.
Syed Abbas Ali, et al., "T cells expressing an anti-B-cell maturation antigen chimeric antigen receptor cause remissions of multiple myeloma", Blood, Sep. 29, 2016, vol. 128, No. 13, pp. 1688-1700.
Marcela V. Maus, et al., "T cells expressing chimeric antigen receptors can cause anaphylaxis in humans", Cancer Immunol Res. Jul. 2013, 1: 26-31.
Robert Berahovich, et al., "CAR-T Cells Based on Novel BCMA Monoclonal Antibody Block Multiple Myeloma Cell Growth", Cancers, 2018, 10, 323.

*Primary Examiner* — Lei Yao
(74) *Attorney, Agent, or Firm* — Perkins Coie LLP; Viola Kung

(57) ABSTRACT

The present invention is directed to a monoclonal anti-human BCMA antibody, or a single-chain variable fragment (scFv), comprising $V_H$ having the amino acid sequence of SEQ ID NO: 6 and $V_L$ having the amino acid sequence of SEQ ID NO: 7. The present invention is also directed to a BCMA chimeric antigen receptor (CAR) comprising from N-terminus to C-terminus: (i) a single-chain variable fragment (scFv) of the present invention, (ii) a transmembrane domain, (iii) at least one co-stimulatory domains, and (iv) an activating domain. The monoclonal antibody of the present invention exhibits selective and high-affinity binding to BCMA. BCMA CAR-T cells based on BCMA scFv of the present invention significantly decreases multiple myeloma tumor growth in an animal model.

9 Claims, 10 Drawing Sheets
Specification includes a Sequence Listing.

```
       10          20         30         40         50
MLQMAGQCSQ  NEYFDSLLHA CIPCQLRCSS NTPPLTCQRY CNASVTNSVK
       60          70         80         90        100
GTNAILWTCL  GLSLIISLAV FVLMFLLRKI NSEPLKDEFK NTGSGLLGMA
      110         120        130        140        150
NIDLEKSRTG  DEIILPRGLE YTVEECTCED CIKSKPKVDS DHCFPLPAME
      160         170        180
EGATILVTTK  TNDYCKSLPA ALSATEIEKS ISAR
```

BCMA-CAR-T CELLS

This application is a continuation of PCT/US2019/023884, filed Mar. 25, 2019; which claims the priority of U.S. Provisional Application No. 62/652,202, filed Apr. 3, 2018. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 25, 2019, and a size of 15.9 kilobytes. The Sequence Listing filed via EFS-Web is part of the specification and is hereby incorporated in its entirety by reference herein.

FIELD OF THE INVENTION

The present invention relates to B cell maturation antigen (BCMA)-specific antibody specifically recognizing BCMA antigen and BCMA-CAR-T Cells, which is useful in the field of adoptive immunity gene therapy for tumors.

BACKGROUND OF THE INVENTION

Multiple myeloma is a cancer of plasma cells characterized by clonal proliferation in the bone marrow microenvironment. Multiple myeloma is the second-most common hematologic malignancy, accounting for 5-10% of all hematologic malignancies in the USA. Despite recent progress in treatment, multiple myeloma remains incurable with high rates of relapsed and refractory 34 disease.

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CAR (Chimeric antigen receptor) constructs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug")[1, 3, 4].

CARs typically consist of a monoclonal antibody-derived single-chain variable fragment (scFv) at the N-terminal part, hinge, transmembrane domain and a number of intracellular co-activation domains: (i) CD28, (ii) CD137 (4-1BB), CD27, (iii) GITR or other co-stimulatory domains, in tandem with an activation CD3-zeta domain. (FIG. 1) [1, 2]. The evolution of CARs is shown in FIG. 1, which went from first generation (with no co-stimulation domains) to second generation (with one co-stimulation domain) to third generation CAR (with several co-stimulation domains). Generating CARs with two costimulatory domains (the so-called $3^{rd}$ generation CAR) have led to increased cytolytic CAR-T cell activity, improved persistence of CAR-T cells leading to its augmented antitumor activity.

Natural killer cells, or NK cells, are a type of cytotoxic lymphocyte critical to the innate immune system. The role NK cells play is analogous to that of cytotoxic T cells in the vertebrate adaptive immune response. NK cells provide rapid responses to virus-infected cells, acting at around 3 days after infection, and respond to tumor formation.

B cell maturation antigen (BCMA) is a cell surface receptor, also known as CD269 and tumor necrosis factor receptor superfamily member 17 (TNFRSF17), that is encoded by TNFRSF17 gene. This receptor is expressed mainly in mature B lymphocytes and in most cases of multiple myeloma (MM) [3].

BRIEF DESCRIPTION OF THE DRAWINGS

FIG. 11A: BCMA CAR-T cells, mock CAR-T cells and non-transduced T cells were added to monolayers of CHO cells and CHO-BCMA cells, and the impedance (i.e., integrity) of the monolayers was monitored over time. Quantitation of cytotoxicity is show with 3 replicates. *p<0.0001 for BCMA CAR-T cells vs mock CAR-T cells and non-transduced T cells. FIG. 11B: The levels of IFN-γ released into the RTCA medium was measured by ELISA; *p<0.0001 for BCMA CAR-T cells vs mock CAR-T cells and non-transduced T cells.

DETAILED DESCRIPTION OF THE INVENTION

Definitions

Figure 1:
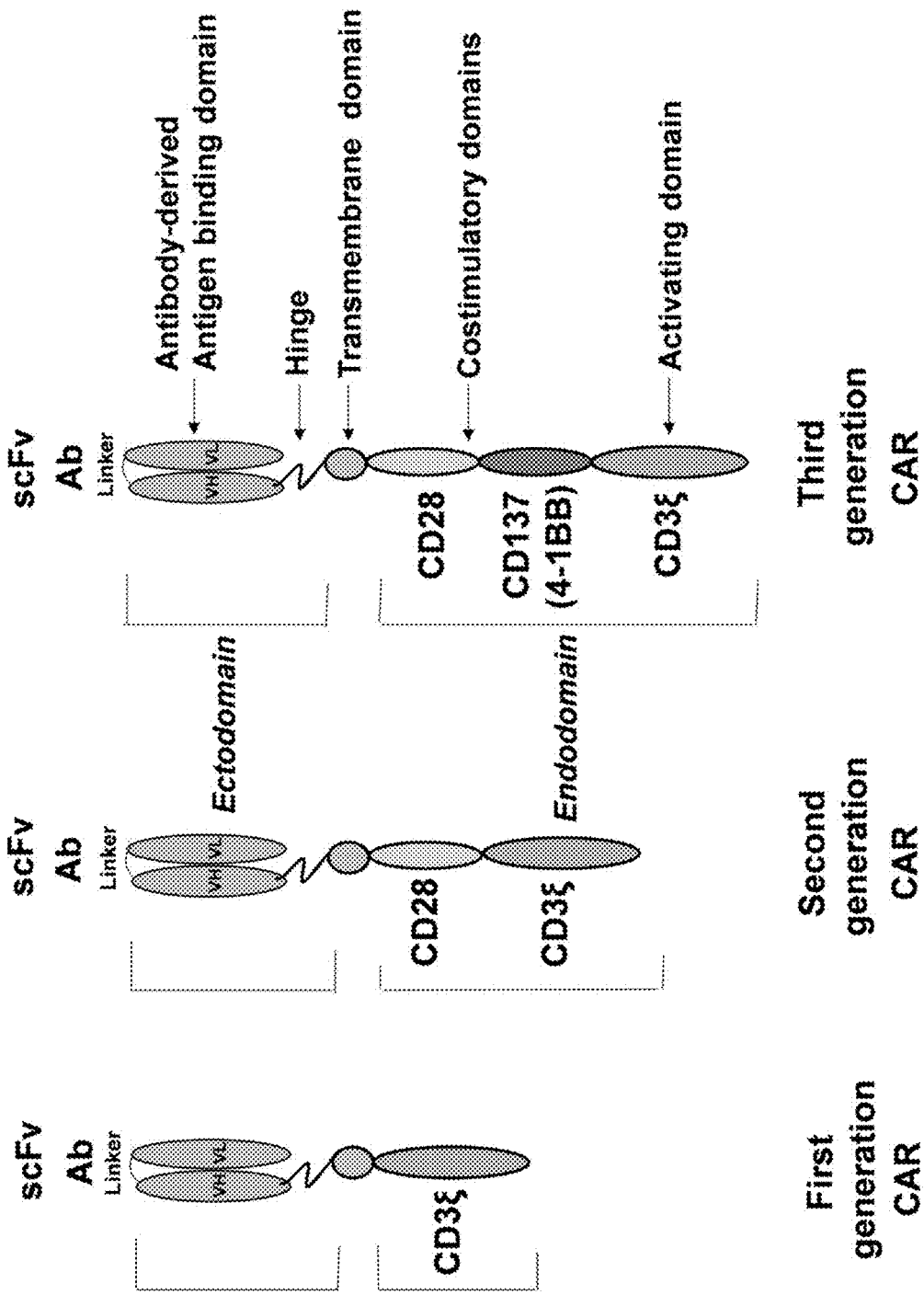
FIG. 1 shows the structures of CAR [6]. On the left panel, it shows the structure of first generation (no costimulatory domains). On the middle panel, it shows the second generation (one co-stimulation domain CD28 or 4-BB). On the right panel, it shows the third generation of CAR (two or several co-stimulation domains).

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a structure independently of other regions.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for engineering an scFv are known to a person skilled in the art.

As used herein, a "tumor antigen" means a biological molecule having antigenicity, expression of which causes cancer.

The human BCMA protein consists of 184 amino-acids: 1-54: extracellular domain; 55-77: transmembrane domain; 78-184: cytoplasmic domain. The amino-acid sequence of BCMA is shown on FIG. 2 with extracellular domain underlined. BCMA lacks signaling peptide and resembles other receptors such as BAFF receptor, transmembrane activator, cyclophilin ligand interactor and calcium modulator (TACI) [4]. These receptors play major role in B cell maturation and differentiation into plasma cells. Their ligands include BAFF and APRIL which expression are increased in MM patients [4]. Monoclonal antibodies target receptor-ligand interactions, and CAR-T cell therapy binds BCMA and kill MINI cells. BCMA also interacts with TRAF1,2,3,5 and 6.

Immunogen for creating BCMA antibody was sequenced from extracellular domain recombinant protein. The inventors have generated mouse anti-human monoclonal antibody specifically targeting BCMA. The inventors have produced BCMA-CAR-T cells to target cancer cells overexpressing BCMA tumor antigen. The BCMA-CAR-T cells of the present invention secrete high level of cytokines against multiple myeloma cancer cells.

The present invention is directed to a monoclonal anti-human BCMA antibody clone (Clone 4C8A) comprising $V_H$ having the amino acid of SEQ ID NO: 6 and $V_L$ having the amino acid of SEQ ID NO: 7, respectively. The monoclonal anti-human BCMA antibody clones were generated against whole length extracellular domain of human BCMA protein (see FIG. 2, underlined sequence). In one embodiment, the monoclonal anti-human BCMA antibody is a single-chain variable fragment (scFv).

The present invention is also directed to a chimeric antigen receptor fusion protein comprising from N-terminus to C-terminus: (i) a single-chain variable fragment (scFv) against BCMA (the present invention), (ii) a transmembrane domain, (iii) at least one co-stimulatory domains, and (iv) an activating domain.

ScFv can be VH-linker-VL or VL-linker-VH.

In one embodiment, the co-stimulatory domain is selected from the group consisting of CD28, 4-1BB, GITR, ICOS-1, CD27, OX-40 and DAP10. A preferred the co-stimulatory domain is CD28.

A preferred activating domain is CD3 zeta (CD3 Z or CD3ζ)

The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain. In one embodiment, a linker sequence having a glycine-serine continuous sequence can be used.

The present invention provides a nucleic acid encoding the BCMA CARs. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

A nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. A virus vector lacking the replicating ability so as not to self-replicate in an infected cell is preferably used.

For example, when a retrovirus vector is used, a suitable packaging cell based on a LTR sequence and a packaging signal sequence possessed by the vector can be selected for preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

A CAR-T cell binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and it may further comprise a suitable excipient.

The inventors have generated a BCMA-specific mAb, clone 4C8A, and characterized it in vitro. Clone 4C8A exhibited selective and high-affinity binding to BCMA, and was used to construct a single-chain variable fragment (scFv). The inventors inserted the 4C8A scFv into a second-generation CAR, generated CAR-T cells, and measured their activity against multiple myeloma cells in vitro and in a mouse xenograft tumor model. The inventors demonstrate that BCMA CAR-T cells based on mAb 4C8A significantly decreased multiple myeloma tumor growth, indicating BCMA CAR-T cells can treat patients with multiple myeloma.

The inventors have generated BCMA-ScFv-CD28-CD3 zeta-CAR-T (BCMA-CAR-T) cells and used them against multiple myeloma cells (MM). BCMA-CAR-T cells secreted high levels of cytokines and were positive by lactate dehydrogenase (LDH) cytotoxicity assay, which indicates killing activity of CAR-T cells against target cancer cells with cytotoxic activity against tumor or viral antigens.

The advantages of the mouse anti-human BCMA monoclonal antibody and the BCMA-ScFv of the present invention include high specificity and high binding affinity ($KD>10^{-10}$) against BCMA-positive multiple myeloma (MM) cancer cell. The BCMA antibody of the present invention is highly potent as a therapeutic agent in many clinical applications.

The present BCMA antibody detects BCMA in BCMA-positive MM cancer cells.

The present BCMA antibody can be used for immunotherapy applications: toxin/drug-conjugated antibody, monoclonal therapeutic antibody, humanization of BCMA antibody, and CAR-T cell immunotherapy.

BCMA antibody can be used with another tumor antigen for generation of bi-specific CARs (for example BCMA-CS1, BCMA-CD38, BCMA-CD33 and other).

BCMA-CAR-T cells using the present BCMA antibody can effectively target BCMA antigen in BCMA-positive cancer cell lines.

BCMA-CAR-T can be used in combination with other therapies such as checkpoint inhibitors, targeted therapies, small molecule inhibitors, and antibodies.

BCMA antibody can be modified with site-directed mutagenesis for affinity tuning; it can be used for humanization and for complete human antibody generation.

BCMA-CAR-T cells can be used clinically against BCMA-positive cancer cells.

Modifications of co-activation domains: CD28, 4-1BB, GITR and others can be used to increase the efficacy of BCMA-CAR. Tag-conjugated BCMA scFv can be used for CAR generation.

Third generation CAR-T or other co-activation signaling domains can be used for the same BCMA-scFv inside CAR.

BCMA CAR can be combined with CARs targeting other tumor antigens or tumor microenvironment, e.g., VEGFR-1-3, PDL-1, bi-specific antibodies (e.g., BCMA and CD3) for therapy.

BCMA-CAR-T cells can be used against cancer stem cells that are resistant against chemotherapy and form aggressive tumors.

BCMA-CAR can be used for generating other types of cells such as CAR-natural killer (NK) cells, BCMA-CAR-macrophages, and other BCMA-CAR hematopoietic cells, which can target BCMA-positive cancers. The present invention provides T cells, or NK cells, or macrophages, or hematopoietic cells, modified to express the BCMA-CAR.

The present invention is useful in treating a mammal subject, such as humans, horses, dogs and cats. The present invention is particularly useful in treating humans.

The following examples further illustrate the present invention. These examples are intended merely to be illustrative of the present invention and are not to be construed as being limiting.

EXAMPLES

Example 1. Hybridoma

We generated mouse monoclonal anti-human BCMA antibody using hybridoma. The hybridoma was generated against BCMA extracellular domain peptide. The hybridoma technology is standard and published [5]. The antibody is IgG 1 type and binds to extracellular domain of BMCA. The sequences of VH and VL and scFv is shown in Example 2.

Example 2. BCMA VH and VL and ScFv Sequences

BCMA scFv was obtained by sequencing hybridoma clones 4C8A4 and 4C8A10 positive for BCMA. The structure of BCMA scFv clone A is: VH-linker-VL. Linker is G4S×3

The bold highlights the nucleotide sequence of $V_H$ (SEQ ID NO: 2) of BCMA antibody Clone 4C8A; the underlined highlights the nucleotide sequence of $V_L$ (SEQ ID NO: 3); in between (italicized) is the nucleotide sequence (SEQ ID NO: 4) encoding a linker.

GTCCAGCTGCAGCAGTCTGGACCTGAGCTGGTAAAGCCTGGGGCTTCA

GTGAAGATGTCCTGCAAGGCTTCTGGATACACATTCACTAGCTATGTT

ATGCACTGGGTGAAGCAGAAGCCTGGGCAGGGCCTTGAGTGGATTGGA

TATATTATTCCTTACAATGATGCTACTAAGTACAATGAGAAGTTCAAA

GGCAAGGCCACACTGACTTCAGACAAATCCTCCAGCACAGCCTACATG

GAGCTCAGCAGCCTGACCTCTGAGGACTCTGCGGTCTATTACTGTGCA

CGCTATAATTACGACGGGTACTTCGATGTCTGGGGCGCAGGGACCACG

GTCACCGTCTCCTCA *GGTGGCGGTGGTTCT* *GGTGGCGGTGGTTCT*

*GGTGGCGGTGGTTCT* GACATTGTGATGACTCAGTCTCCAGCCACCCT

GTCTGTGACTCCAGGAGATAGAGTCTCTCTTTCCTGCAGGGCCAGCCA

GAGTATTAGCGACTACTTACACTGGTATCAACAAAAATCACATGAGTC

TCCAAGGCTTCTCATCAAATATGCTTCCCAATCCATCTCTGGGATCCC

CTCCAGGTTCAGTGGCAGTGGATCAGGGTCAGATTTCACTCTCAGTAT

CAACAGTGTGGAACCTGAAGATGTTGGAGTGTATTACTGTCAAAATGG

TCACAGCTTTCCTCCGACGTTCGGTGGAGGCACCAAGCTGGAAATCAA

A

BCMA scFv (BCMA clone 4C8A) Protein:

(SEQ ID NO: 5)

V Q L Q Q S G P E L V K P G A S V K M S C K A S

G Y T F T S Y V M H W V K Q K P G Q G L E W I G

Y I I P Y N D A T K Y N E K F K G K A T L T S D

K S S S T A Y M E L S S L T S E D S A V Y Y C A

R Y N Y D G Y F D V W G A G T T V T V S S *G G G*

*G S G G G G S G G G G S* D I V M T Q S P A T L S

V T P G D R V S L S C R A S Q S I S D Y L H W Y

Q Q K S H E S P R L L I K Y A S Q S I S G I P S

R F S G S G S G S D F T L S I N S V E P E D V G

V Y Y C Q N G H S F P P T F G G G T K L E I K

In the protein, the bold highlights the amino acid sequence of $V_H$ (SEQ ID NO: 6); the underlined highlights the amino sequence of $V_L$ (SEQ ID NO: 7); in between (italicized) is the amino acid sequence of 3×G4S linker GGGGSGGGGSGGGGS sequence (SEQ ID NO: 8).

Example 3. BCMA-CAR Sequences

Figures 2, 3:
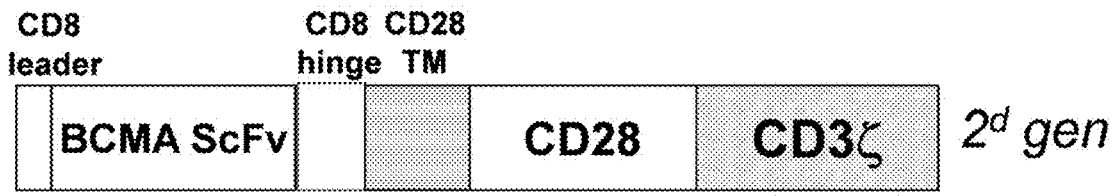
FIG. 2 show the amino-acid sequence of BCMA protein (SEQ ID NO: 1); the extracellular domain is underlined.
FIG. 3 shows the structure of BCMA CAR construct (second generation).

The scheme of BCMA-CAR construct is shown on FIG. 3. Lentiviral vector Lenti CMV-MCS-EF1a-puro, was used for cloning of all scFv CAR sequences.

The following nucleotide sequence shows CD8 leader-BCMA ScFv-CD8 hinge-TM28-CD28-CD3 zeta of the present invention. The CAR structure includes Human CD8 signaling peptide, BCMA scFv ($V_H$-Linker 3×(G4S)-$V_L$), CD8 hinge, CD28 transmembrane, activation domains, CD3 zeta (FIG. 3).

CD8 leader sequence-BCMA scFv ($V_H$-Linker-$V_L$)-CD8 hinge-CD28 TM-CD28-CD3-zeta:

```
<CD8 leader)>,
                                      SEQ ID NO: 9
ATGGCCTTACCAGTGACCGCCTTGCTCCTGCCGCTGGCCTTGCTGCTC

CACGCCGCCAGGCCG

<Nhe I restriction site>
gctagc

<BCMA, Clone 4C8A4 scFv>,
                                     SEQ ID NO: 10
GTCCAGCTGCAGCAGTCTGGACCTGAGCTGGTAAAGCCTGGGGCTTCA

GTGAAGATGTCCTGCAAGGCTTCTGGATACACATTCACTAGCTATGTT

ATGCACTGGGTGAAGCAGAAGCCTGGGCAGGGCCTTGAGTGGATTGGA

TATATTATTCCTTACAATGATGCTACTAAGTACAATGAGAAGTTCAAA

GGCAAGGCCACACTGACTTCAGACAAATCCTCCAGCACAGCCTACATG

GAGCTCAGCAGCCTGACCTCTGAGGACTCTGCGGTCTATTACTGTGCA

CGCTATAATTACGACGGGTACTTCGATGTCTG GGGCGCAGGGACCAC

GGTCACCGTCTCCTCA GGTGGCGGTGGTTCT GGTGGCGGTGGTTCT

GGTGGCGGTGGTTCT GACATTGTGATGACTCAGTCTCCAGCCACCCT

GTCTGTGACTCCAGGAGATAGAGTCTCTCTTTCCTGCAGGGCCAGCCA

GAGTATTAGCGACTACTTACACTGGTATCAACAAAAATCACATGAGTC

TCCAAGGCTTCTCATCAAATATGCTTCCCAATCCATCTCTGGGATCCC

CTCCAGGTTCAGTGGCAGTGGATCAGGGTCAGATTTCACTCTCAGTAT

CAACAGTGTGGAACCTGAAGATGTTGGAGTGTATTACTGTCAAAATGG

TCACAGCTTTCCTCCGACGTTCGGTGGAGGCACCAAGCTGGAAATCAA

A
```

-continued

<XhoI restriction site>
CTCGAG

<CD8 hinge>,
SEQ ID NO: 11
AAGCCCACCACGACGCCAGCGCCGCGACCACCAACACCGGCGCCCACC

ATCGCGTCGCAGCCCCTGTCCCTGCGCCCAGAGGCGAGCCGGCCAGCG

GCGGGGGGCGCAGTGCACACGAGGGGGCTGGACTTCGCCAGTGATaag ccc

<CD28 TM/activation>,
SEQ ID NO: 12
TTTTGGGTGCTGGTGGTGGTTGGTGGAGTCCTGGCTTGCTATAGCTTG

CTAGTAACAGTGGCCTTTATTATTTTCTGGGTGAGGAGTAAGAGGAGC

AGGCTCCTGCACAGTGACTACATGAACATGACTCCCCGCCGCCCCGGG

CCCACCCGCAAGCATTACCAGCCCTATGCCCCACCACGCGACTTCGCA

GCCTATCGCTCC

<CD3 zeta>,
SEQ ID NO: 13
AGAGTGAAGTTCAGCAGGAGCGCAGACGCCCCCGCGTACCAGCAGGGC

CAGAACCAGCTCTATAACGAGCTCAATCTAGGACGAAGAGAGGAGTAC

GATGTTTTGGACAAGAGACGTGGCCGGGACCCTGAGATGGGGGAAAG

CCGCAGAGAAGGAAGAACCCTCAGGAAGGCCTGTACAATGAACTGCAG

AAAGATAAGATGGCGGAGGCCTACAGTGAGATTGGGATGAAAGGCGAG

CGCCGGAGGGGCAAGGGGCACGATGGCCTTTACCAGGGTCTCAGTACA

GCCACCAAGGACACCTACGACGCCCTTCACATGCAGGCCCTGCCCCCT

CGCTAATAG

<EcoRI restriction site>
gaattc

Nucleotide sequence of BCMA-CAR
(SEQ ID NO: 14)
ATGGCCTTACCAGTGACCGCCTTGCTCCTGCCGCTGGCCTTGCTGCTC CACGCCGCCAGGCCGgctagc GTCCAGCTGCAGCAGTCTGGACCTGA

GCTGGTAAAGCCTGGGGCTTCAGTGAAGATGTCCTGCAAGGCTTCTGG

ATACACATTCACTAGCTATGTTATGCACTGGGTGAAGCAGAAGCCTGG

GCAGGGCCTTGAGTGGATTGGATATATTATTCCTTACAATGATGCTAC

TAAGTACAATGAGAAGTTCAAAGGCAAGGCCACACTGACTTCAGACAA

ATCCTCCAGCACAGCCTACATGGAGCTCAGCAGCCTGACCTCTGAGGA

CTCTGCGGTCTATTACTGTGCACGCTATAATTACGACGGGTACTTCGA

TGTCTG GGGCGCAGGGACCACGGTCACCGTCTCCTCA GGTGGCGGT

GGTTCT GGTGGCGGTGGTTCT GGTGGCGGTGGTTCT GACATTGTG

ATGACTCAGTCTCCAGCCACCCTGTCTGTGACTCCAGGAGATAGAGTC

TCTCTTTCCTGCAGGGCCAGCCAGAGTATTAGCGACTACTTACACTGG

TATCAACAAAATCACATGAGTCTCCAAGGCTTCTCATCAAATATGCT

TCCCAATCCATCTCTGGGATCCCCTCCAGGTTCAGTGGCAGTGGATCA

GGGTCAGATTTCACTCTCAGTATCAACAGTGTGGAACCTGAAGATGTT

GGAGTGTATTACTGTCAAAATGGTCACAGCTTTCCTCCGACGTTCGGT

GGAGGCACCAAGCTGGAAATCAAActcgagAAGCCCACCACGACGCCA

GCGCCGCGACCACCAACACCGGCGCCCACCATCGCGTCGCAGCCCCTG

TCCCTGCGCCCAGAGGCGAGCCGGCCAGCGGCGGGGGGCGCAGTGCAC

ACGAGGGGGCTGGACTTCGCCAGTGATaagccctttttgggtgctggtg gtggttggtggagtcctggcttgctatagatgctagtaacagtggcct ttattattttctgggtgaggagtaagaggagcaggctcctgcacagtg actacatgaacatgactccccgccgccccgggcccacccgcaagcatt accagccctatgccccaccacgcgacttcgcagcctatcgctccAGAG

TGAAGTTCAGCAGGAGCGCAGACGCCCCCGCGTACCAGCAGGGCCAGA

ACCAGCTCTATAACGAGCTCAATCTAGGACGAAGAGAGGAGTACGATG

TTTTGGACAAGAGACGTGGCCGGGACCCTGAGATGGGGGAAAGCCGC

AGAGAAGGAAGAACCCTCAGGAAGGCCTGTACAATGAACTGCAGAAAG

ATAAGATGGCGGAGGCCTACAGTGAGATTGGGATGAAAGGCGAGCGCC

GGAGGGGCAAGGGGCACGATGGCCTTTACCAGGGTCTCAGTACAGCCA

CCAAGGACACCTACGACGCCCTTCACATGCAGGCCCTGCCCCCTCGCT

AAtag

Translated amino-acid sequence of BCMA-CAR protein (see FIG. 3 for construct structure) comprises BCMA scFv protein of SEQ ID NO: 5.

Example 4. BCMA Antibody Specifically Detect BCMA Antigen by ELISA Assay

Figure 4:
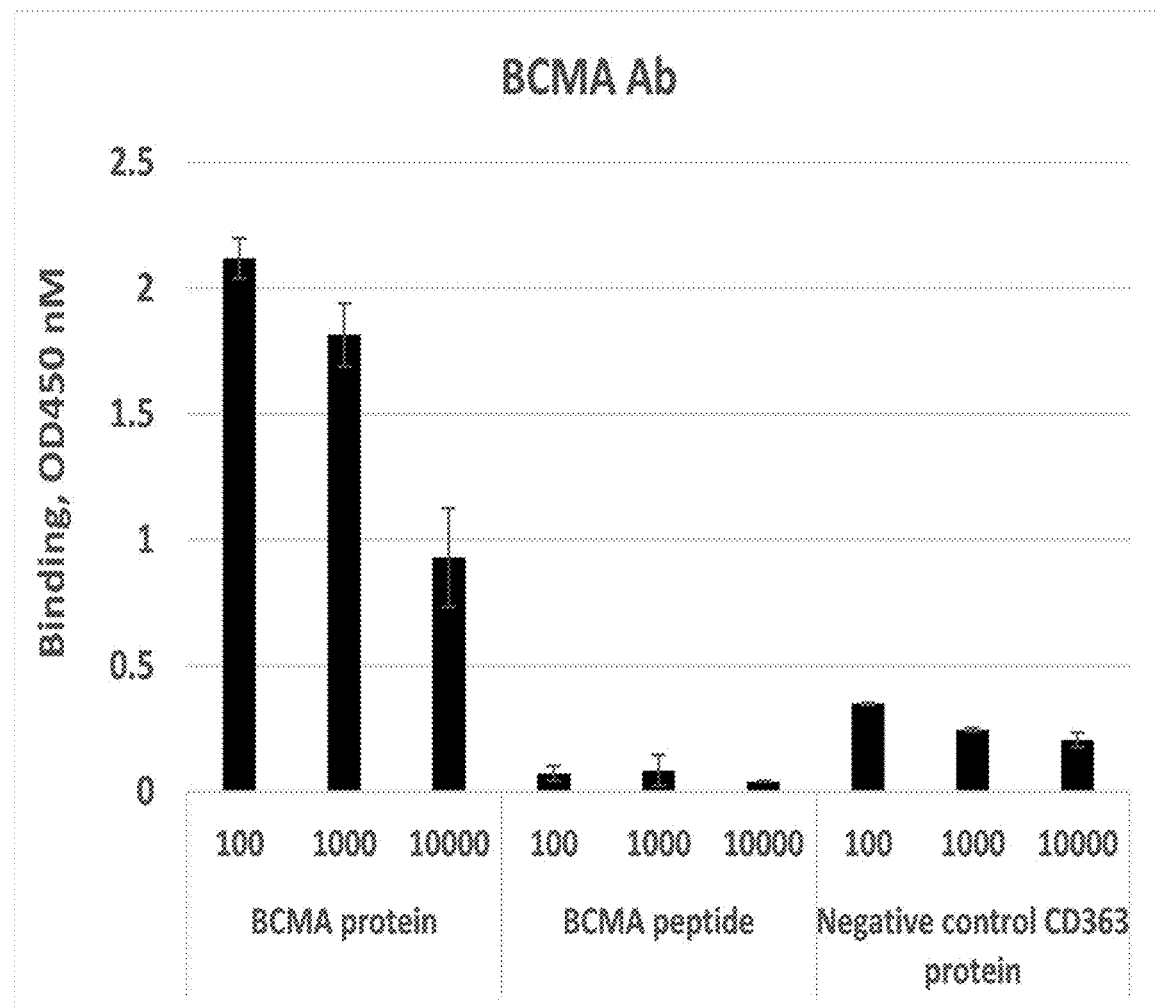
FIG. 4 shows that BCMA antibody binds to BCMA protein but not to a shorter peptide from BCMA extracellular domain or to a negative control CD363 protein in an ELISA assay. The binding of BCMA antibody to BCMA antigen was specific and increased in a dose-dependent manner. Student's t-test shows significant binding of BCMA antibody to BCMA protein, *p<0.0001 for BCMA protein vs BCMA peptide and control.

We generated mouse monoclonal anti-human BCMA monoclonal antibody 4C8A using hybridoma. Dilutions of the antibody were incubated in ELISA plates coated with BCMA protein, or BCMA peptide (BCMA extracellular domain protein with a C-terminal deletion of 37 residues), or an irrelevant control CD363 protein. Binding of BCMA mAb 4C8A to the coated protein was detected with HRP-conjugated anti-mouse IgG and TMB substrate. The ELISA shows specific binding of hybridoma BCMA Ab to the BCMA antigen, but not to control protein or BCMA shorter peptide. The binding of BCMA to BCMA protein was in a dose-dependent manner: decreased with decreased antibody dilution in contrast to negative controls (FIG. 4).

Example 5. BCMA Antibody has High Affinity to BCMA Protein

Figure 5:
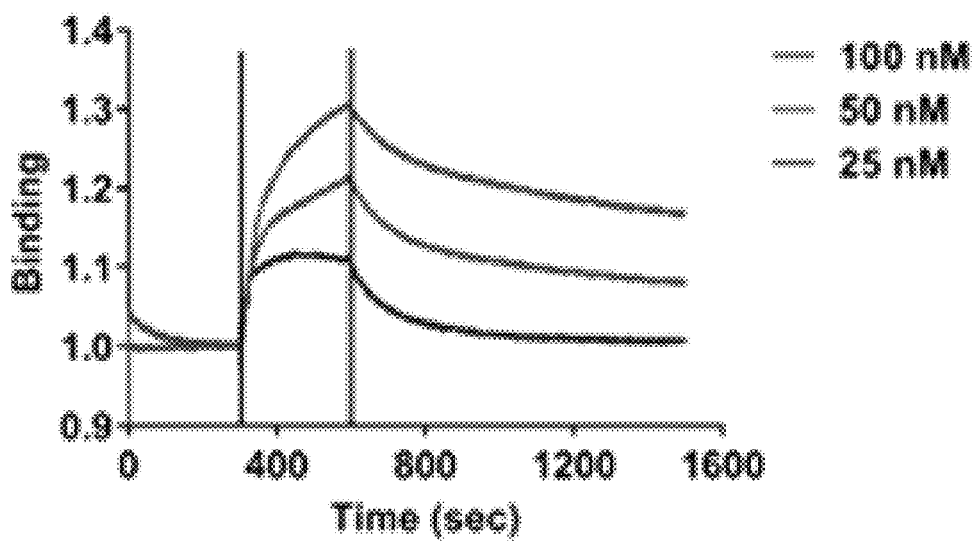
FIG. 5 shows the affinity of BCMA antibody binding to BCMA antigen. BCMA monoclonal antibody (mAb) 4C8A was loaded onto a Blitz mouse Fc capture sensor at 3 concentrations (first vertical bar), then washed out (second vertical bar). Binding was monitored over time by the Blitz station. X-axis, time in seconds; Y-axis, binding of BCMA antibody by BLItz system.

The BCMA 4C8A antibody was diluted to 100, 50 and 25 nM and added to the anti-mouse IgG biosensor (ForteBio Corp., Menlo Park, CA). After 5 minutes, the biosensor was rinsed free of unbound antibody. Binding was monitored by the BLItz system (ForteBio), and the antibody's dissociation constant was determined with the BLItz software. BCMA mAb, clone 4C8A, exhibited strong binding to BCMA, with a Kd of approximately 2.8 nM (FIG. 5).

Example 6. BCMA Antibody Detects Human BCMA Proteins Expressed in 293-BCMA Cells by Immunostaining Cell lines RPMI8226, H929, MM1S, Raji, K562, 293 and CHO were purchased from the ATCC (Manassas, VA) and cultured either in DMEM (GE Healthcare, Chicago, IL) or in RPMI-1640 medium (Thermo Fisher, Waltham, MA)

containing 10% FBS (AmCell, Mountain View, CA). CHO-BCMA cells were purchased from BPS Bioscience (San Diego, CA) and cultured in Ham's F12K medium containing 10% FBS and 1 mg/ml geneticin (Thermo Fisher). Human peripheral blood mononuclear cells (PBMC) were isolated by density sedimentation over Ficoll-Paque (GE Healthcare).

We transfected 293 cells either with BCMA (CD269)-human Fc protein or control CD18 protein fused with human Fc protein and performed immunostaining analysis. BCMA antibody detected BCMA protein expressed on the cell surface but did not detect negative control CD18-human Fc protein demonstrating high specificity of BCMA antibody binding to BCMA inside cells. By IHC, clone 4C8A bound to RPMI8226 cells, myeloma primary tumors and normal human liver, but not to any other normal or other type cancer human tissues, confirming the specificity of BCMA expression. BCMA antibody detected also BCMA in primary multiple myeloma tumors.

Figure 6:
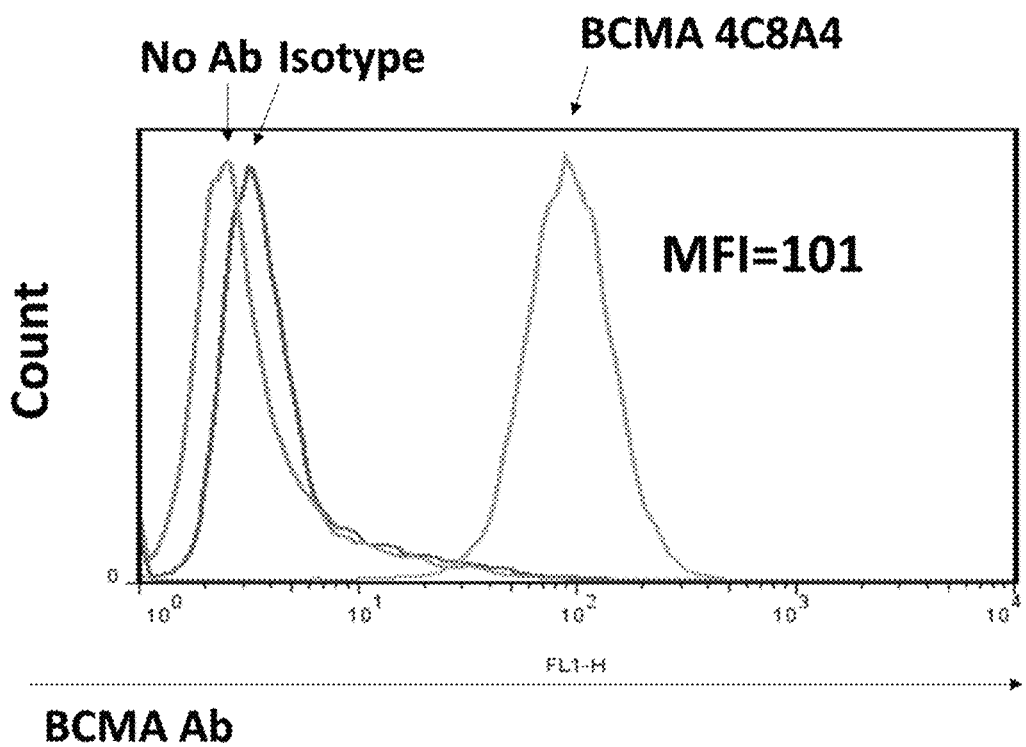
FIG. 6 shows FACS analysis with BCMA antibody using RPMI8226 multiple myeloma cell line. The 4CA8 supernatant from hybridoma was used for FACS analysis. X-axis: BCMA antibody; Y-axis-FACS count.
Figure 7:
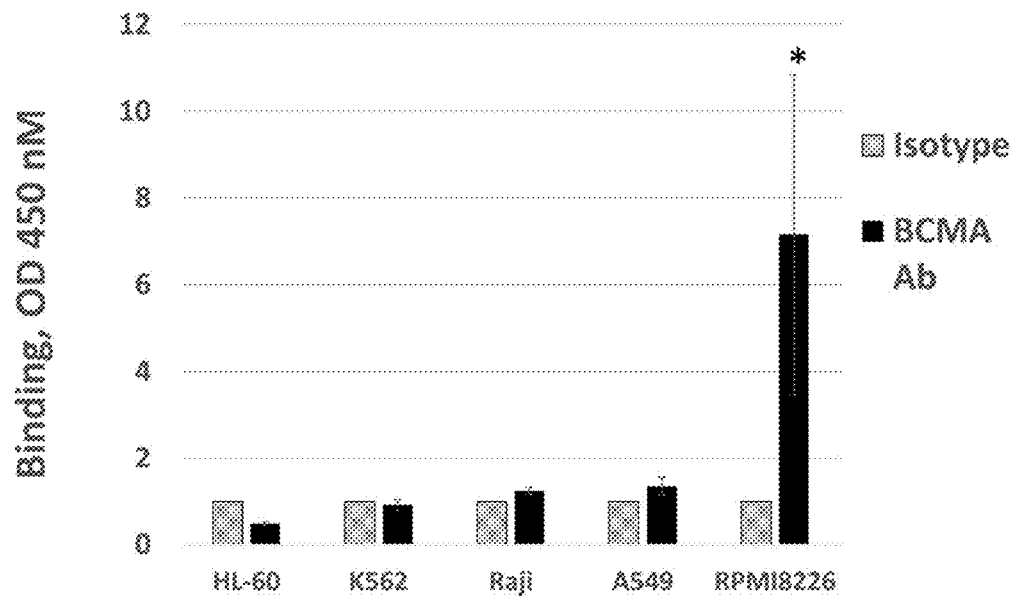
FIG. 7 shows the detection of BCMA in multiple myeloma cell line but not in leukemia or other cancer cell lines. Y-axis: MFI of binding by FACS with isotype antibody or BCMA antibody. X-axis: Cancer cell lines used for FACS with BCMA antibody. Student's t-test, p<0.05.

Example 7. BCMA Antibody Specifically Detects BCMA in Multiple Myeloma Cells by FACS Analysis We performed FACS analysis as described in [6] with BCMA antibody on multiple myeloma RPMI8226 cells (FIG. 6). BCMA antibody detected BCMA in RPMI8226 multiple myeloma cell line (FIG. 6). Then we tested multiple myeloma cell line and several negative control cell lines: leukemia: K562, Raji, HL-60 and lung cancer A549 cell lines (FIG. 7). BCMA detected BCMA in multiple myeloma but not in other cancer cell lines (FIG. 7) demonstrating high specificity of BCMA antibody.

Figure 8:
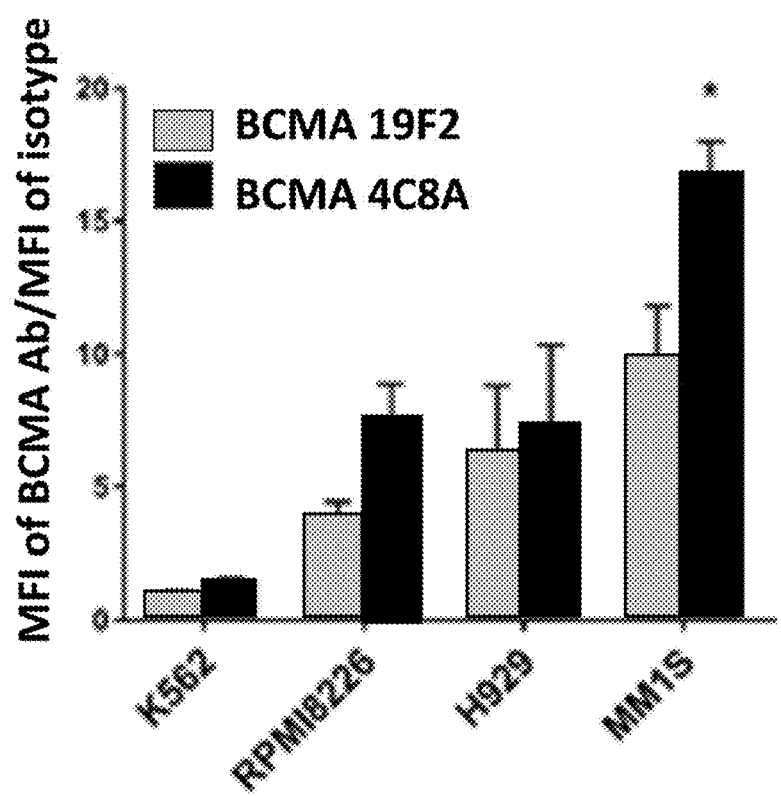
FIG. 8 shows high and specific detection of BCMA with Promab's 4C8A and Biolegend antibody in several multiple myeloma cell lines. BCMA mAb 4C8A, Biolegend BCMA mAb clone number 19F2 and a mouse IgG1 isotype control mAb were incubated with myeloma lines RPMI8226, H929, and MM1S, as well as Burkitt's lymphoma line Raji and the BCMA-negative cell line K562. Binding of the antibodies to the cells was detected by flow cytometry with PE-conjugated anti-mouse IgG. To quantitate the binding in panel E, the mean fluorescence intensity (MFI) of each BCMA mAb was divided by the MFI of the isotype control mAb. Each stain was performed 3-10 times; *p<0.05 for BCMA mAb 4C8A vs BCMA mAb 19F2 in MM1S cells.

Example 8. BCMA Antibody Detects BCMA Antigen Similarly or Better than Commercial BCMA Antibody We sequenced BCMA antibody and the sequences of $V_H$ and $V_L$ and ScFv are shown in Example 2. We purified and isolated BCMA antibody and compared with commercial antibody from Biolegend company (clone number: 19F2). BCMA antibody detected BCMA antigen by FACS analysis comparable or better than Biolegend antibody (FIG. 8).

Example 9. Generation of BCMA-CAR-Lentivirus

The inventors generated BCMA CAR constructs inside lentiviral vector cloned into Xba I and Eco R I sites. The lentiviral CAR construct containing the BCMA ScFv-CD28-CD3zeta insert—between the Xba I and Eco RI cloning sites.

The lentiviruses were generated in 293T cells and titer was established by RT-PCR. Then equal dose of lentiviruses was used for transduction of T cells.

BCMA-CAR-lentivirus was generated as described in (6). In brief, DNA encoding the BCMA CAR was synthesized and subcloned into a third-generation lentiviral vector, Lenti CMV-MCS-EF1a-puro by Syno Biological (Beijing, China). Ten million growth-arrested HEK293FT cells (Thermo Fisher) were seeded into T75 flasks and cultured overnight, then transfected with the pPACKH1 Lentivector Packaging mix (System Biosciences, Palo Alto, CA) and 10 µg of the lentiviral vector using the CalPhos Transfection Kit (Takara, Mountain View, CA). The next day the medium was replaced with fresh medium, and 48 h later the lentivirus-containing medium was collected. The medium was cleared of cell debris by centrifugation at 2100 g for 30 min. The virus particles were collected by centrifugation at 112,000 g for 100 min, suspended in AIM V medium, aliquoted and frozen at −80° C. The titers of the virus preparations were determined by quantitative RT-PCR using the Lenti-X qRT-PCR kit (Takara) according to the manufacturer's protocol and the 7900HT thermal cycler (Thermo Fisher). The lentiviral titers were >1×10$^8$ pfu/ml.

Example 10. Generation of BCMA-CAR-T Cells

BCMA-CAR-T cells were generated as described in [6]. In brief, PBMC were suspended at 1×10$^6$ cells/ml in AIM V-AlbuMAX medium (Thermo Fisher) containing 10% FBS and 10 ng/ml IL-2 (Thermo Fisher), mixed with an equal number (1:1 ratio) of CD3/CD28 Dynabeads (Thermo Fisher), and cultured in non-treated 24-well plates (0.5 ml per well). At 24 and 48 hours, lentivirus was added to the cultures at a multiplicity of infection (MOI) of 5, along with 1 □l of TransPlus transduction enhancer (AlStem). As the T cells proliferated over the next 10-12 days, the cells were counted every 2-3 days and fresh medium with 10 ng/ml IL-2 was added to the cultures to maintain the cell density at 1-3×10$^6$ cells/ml.

Example 11. BCMA-CAR-T Cells Kill Multiple Myeloma Cells and Secrete High Level of IFN-Gamma Against BCMA-Positive Cancer Cells We designed BCMA-CAR-T cells with CAR construct shown in FIG. 3. We used Mock scFv and generated Mock-CAR-T cells as a negative control. BCMA CAR-T cells expressing BCMA scFV were detected after transduction lentiviral BCMA CAR into T cells with BCMA recombinant protein by FACS as described in (6). T cells and Mock CAR-T cells were negative.

We incubated BCMA-CAR-T cells with multiple myeloma cancer cells RPMI8266, HT929 and MINH S cells and performed LDH assay [6] and ELISA with kit from Promega and Fisher, respectively, according to their protocols. K562 cells were used as a negative control. In brief, Target cells (RPMI8226, H929, MM1S, K562) were cultured with the effector cells (CAR-T cells or non-transduced T cells) at a 1:1 ratio (1×10$^4$ cells each) in U-bottom 96-well plates with 200 µl of AIM V-AlbuMAX medium containing 10% FBS, in triplicate. After 16 hours, the top 150 µl of medium was transferred to V-bottom 96-well plates and centrifuged at 300 g for 5 min to pellet any residual cells. The top 120 µl of supernatant was transferred to a new 96-well plate and analyzed by ELISA for human IFN-γ levels using a kit from R&D Systems (Minneapolis, MN) according to the manufacturer's protocol.

Figure 9:
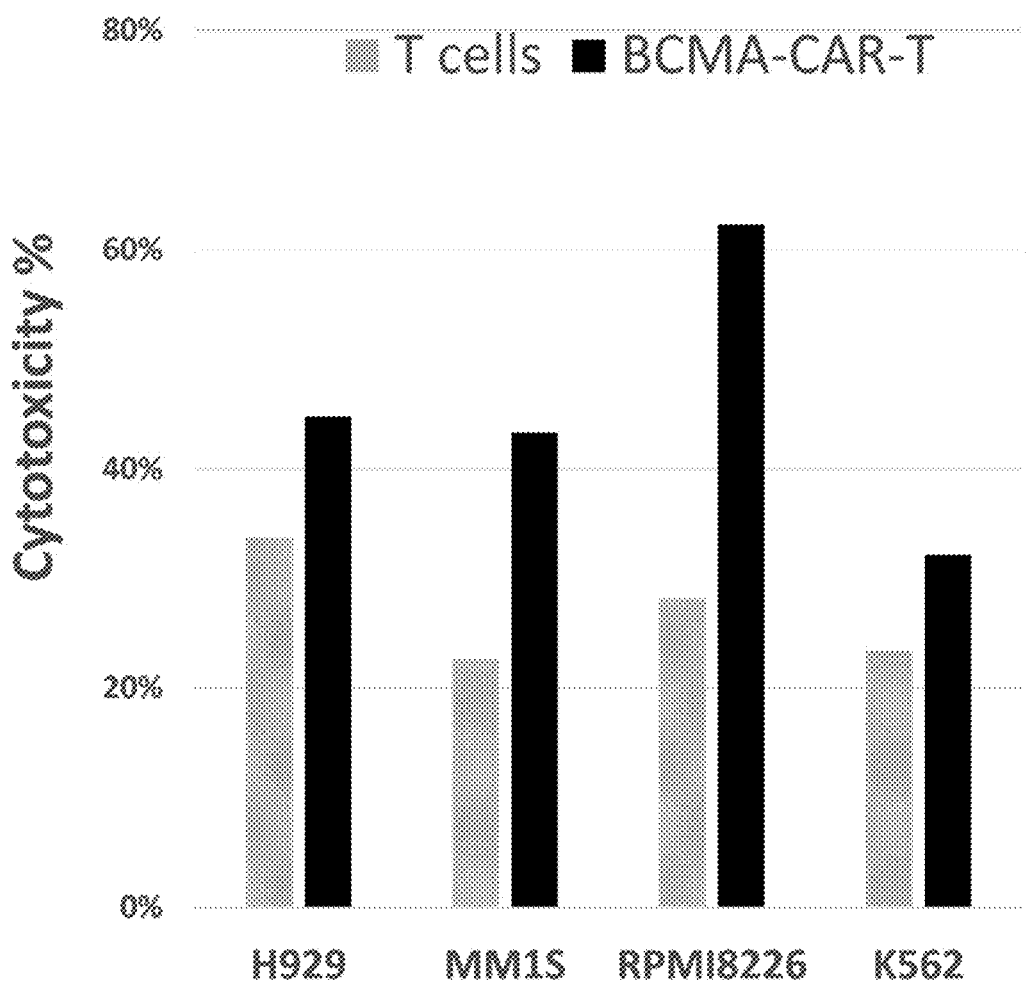
FIG. 9 shows significant killing of multiple myeloma cells by BCMA-CAR-T cells by lactate dehydrogenase (LDH) assay. P<0.05 killing in multiple myeloma cells versus T cells and BCMA-negative K563 cells.
Figure 10:
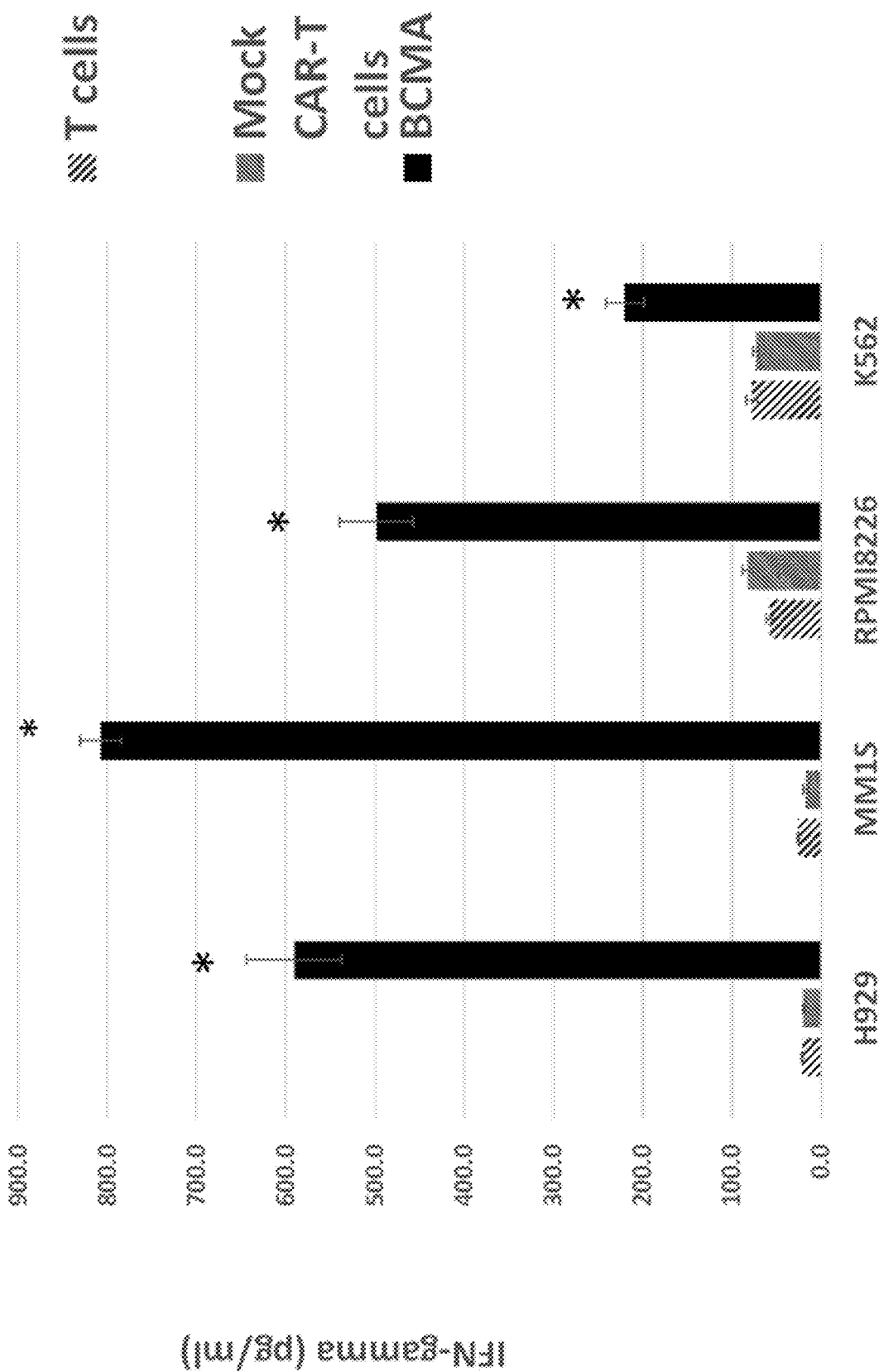
FIG. 10 shows that BCMA-CAR-T cells secreted high level of IFN-gamma in multiple myeloma cells but not in negative control cells. p<0.05 IFN-gamma in multiple myeloma cells versus T and CAR-T cells.

BCMA-CAR-T cells killed RPMI8226, HT929 and MIVI1S cells (FIG. 9) and secreted high level of IFN-gamma against multiple myeloma cancer cells (FIG. 10). The level of killing and secretion of IFN-gamma was significantly higher than with T and Mock CAR-T cells.

Example 12. BCMA-CAR-T Cells Specifically Kill CHO-BCMA Cells

Figures 11A, 11B:
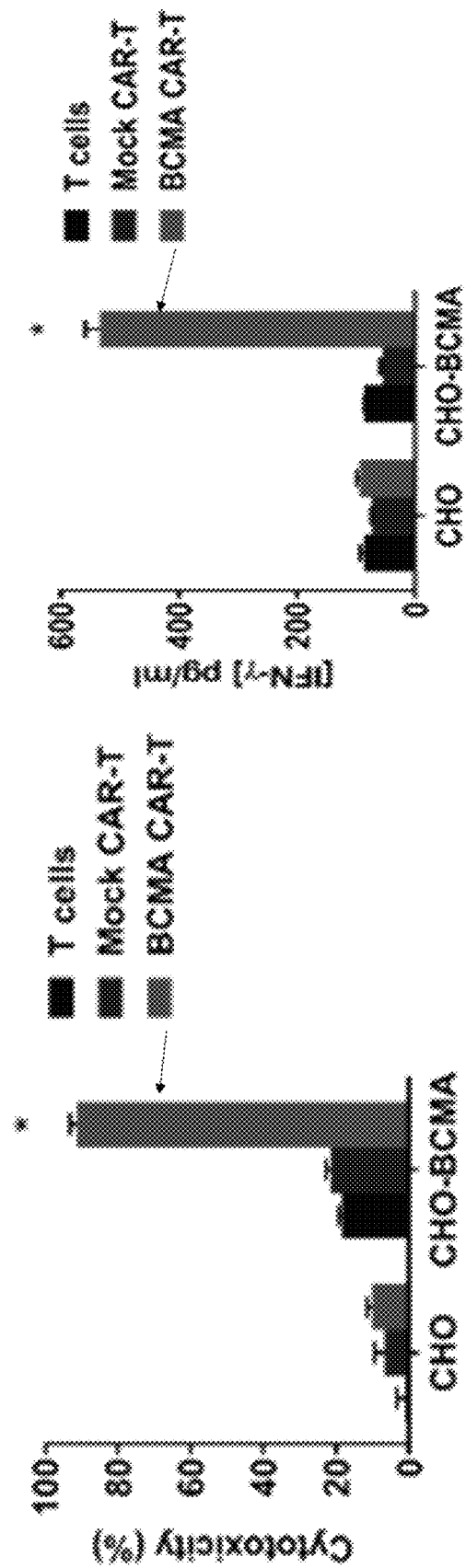
FIGS. 11A and 11B show BCMA-CAR-T cells specifically killed CHO-BCMA cells and secreted significant level of γ-IFN.
Figure 12:
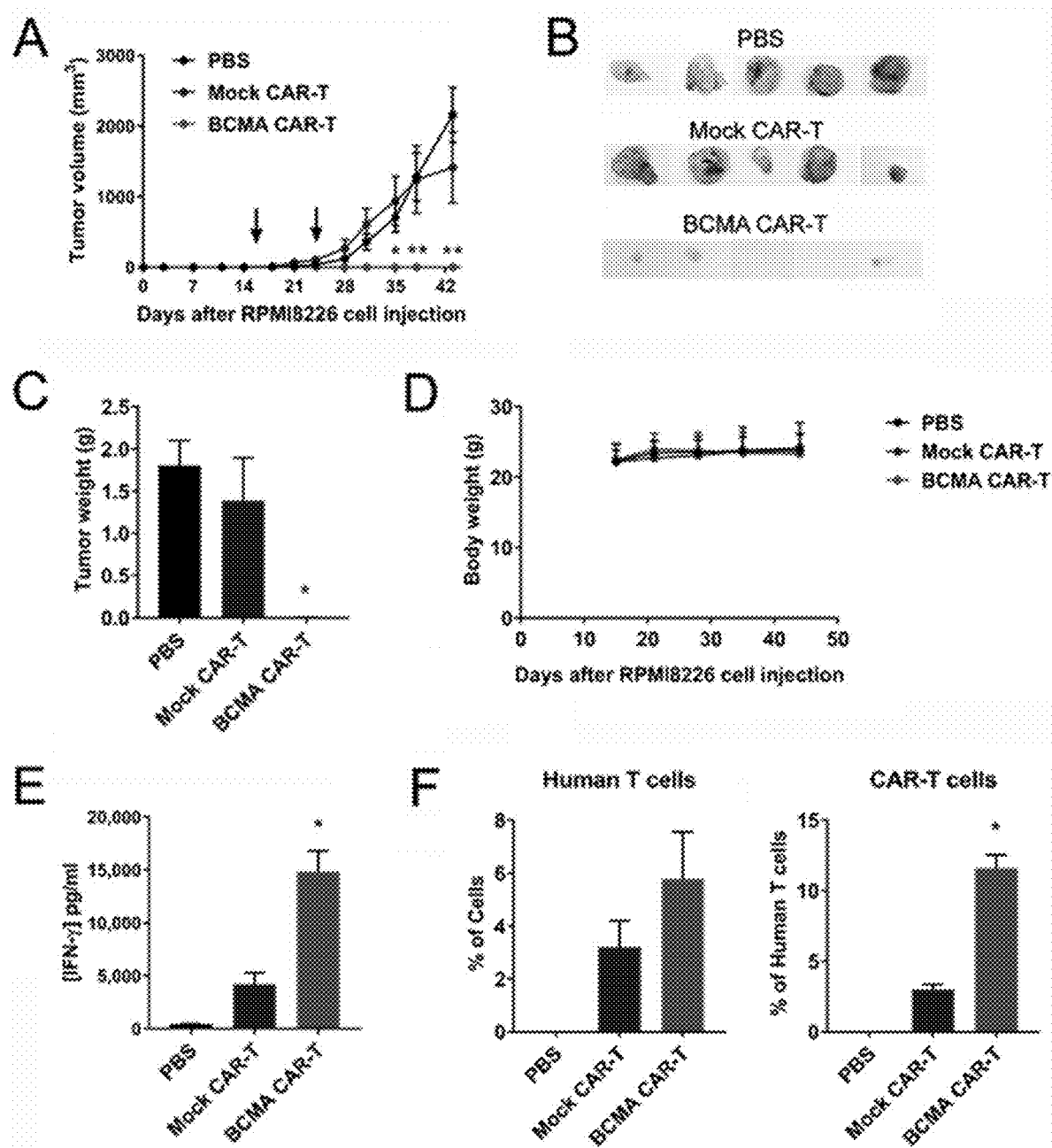
FIG. 12 shows that BCMA CAR-T cells significantly decrease small tumor xenograft mouse tumor growth. A: NSG mice were injected subcutaneously with RPMI8226 myeloma cells and tumor size was measured bi-weekly with calipers. On days 16 and 24 (arrows), the mice received BCMA CAR-T cells, mock CAR-T cells or PBS intravenously; *p<0.01, **p<0.0001 for BCMA CAR-T cells vs mock CAR-T cells and PBS. B: The tumors were excised and photographed. C: The excised tumors were weighed; *p<0.05 for BCMA CAR-T cells vs mock CAR-T cells and PBS. D: The mice were weighed weekly during the study. E: Human IFN-γ levels were measured in the plasma by ELISA at the end of the study; *p<0.0001 for BCMA CAR-T cells vs mock CAR-T cells and PBS. F: The peripheral blood cells were analyzed by flow cytometry at the end of the study for binding to human BCMA protein and an antibody specific for human CD3. The percentage of cells binding to the CD3 mAb is shown on the left, and the percentage of those human T cells that also bound to the BCMA protein is shown on the right; *p<0.0001 for BCMA CAR-T cells vs mock CAR-T cells.

The cytotoxicity assay and IFN-gamma ELISA were performed as described in (6) with BCMA-CAR-T cells in CHO-BCMA and negative control CHO cells. In brief, adherent target cells (CHO or CHO-BCMA) were seeded into 96-well E-plates (Acea Biosciences, San Diego, CA) at 1×10$^4$ cells per well and monitored in culture overnight with the impedance-based real-time cell analysis (RTCA) xCEL-Ligence system (Acea Biosciences). The next day, the medium was removed and replaced with AIM V-AlbuMAX medium containing 10% FBS±1×10$^5$ effector cells (CAR-T cells or non-transduced T cells), in triplicate. The cells in the E-plates were monitored for another 1-2 days with the RTCA system, and impedance was plotted over time. Cytotoxicity was calculated as (impedance of target cells without effector cells−impedance of target cells with effector cells)× 100/impedance of target cells without effector cells. BCMA CAR-T cells, but not mock CAR-T cells or non-transduced cells, substantially decreased the impedance of the CHO-BCMA monolayer, indicative of cytolysis (FIG. 12, left panels). BCMA CAR-T cells did not kill parental CHO cells, indicating that the cytotoxicity for CHO-BCMA cells was BCMA-dependent (FIG. 11A). Analysis of the medium from the RTCA assay indicated that BCMA CAR-T cells produced significant level of IFN-γ in response to CHO-BCMA but not CHO cells (FIG. 11B).

Example 13. BCMA-CAR-T Cells Significantly Decrease RPMI8226 Xenograft Tumor Growth in Mice Model In Vivo BCMA 4C8A CAR-T cells were tested by treating NSG mice with established subcutaneous RPMI8226 tumors. First, CAR-T cells were administered on day 18, when the tumors were approximately 150 mm$^3$, and again six days later. In the mice treated with BCMA CAR-T cells, tumor size decreased in a sustained manner (FIG. 12A); at the end of the study, only 1 tiny tumor was found among the 7 mice (FIG. 12B-C). In the mice treated with PBS or the mock CAR-T cells, tumors continued to enlarge over time (FIG. 12A-C). BCMA CAR-T cells did not affect mouse weight (FIG. 12D). Significantly more human T cells were detected in the bloodstream of BCMA CAR-T cell-treated mice than in mock CAR-T cell-treated mice, and nearly 20% of these human T cells were CAR-T cells (FIG. 12E,F).

Figure 13:
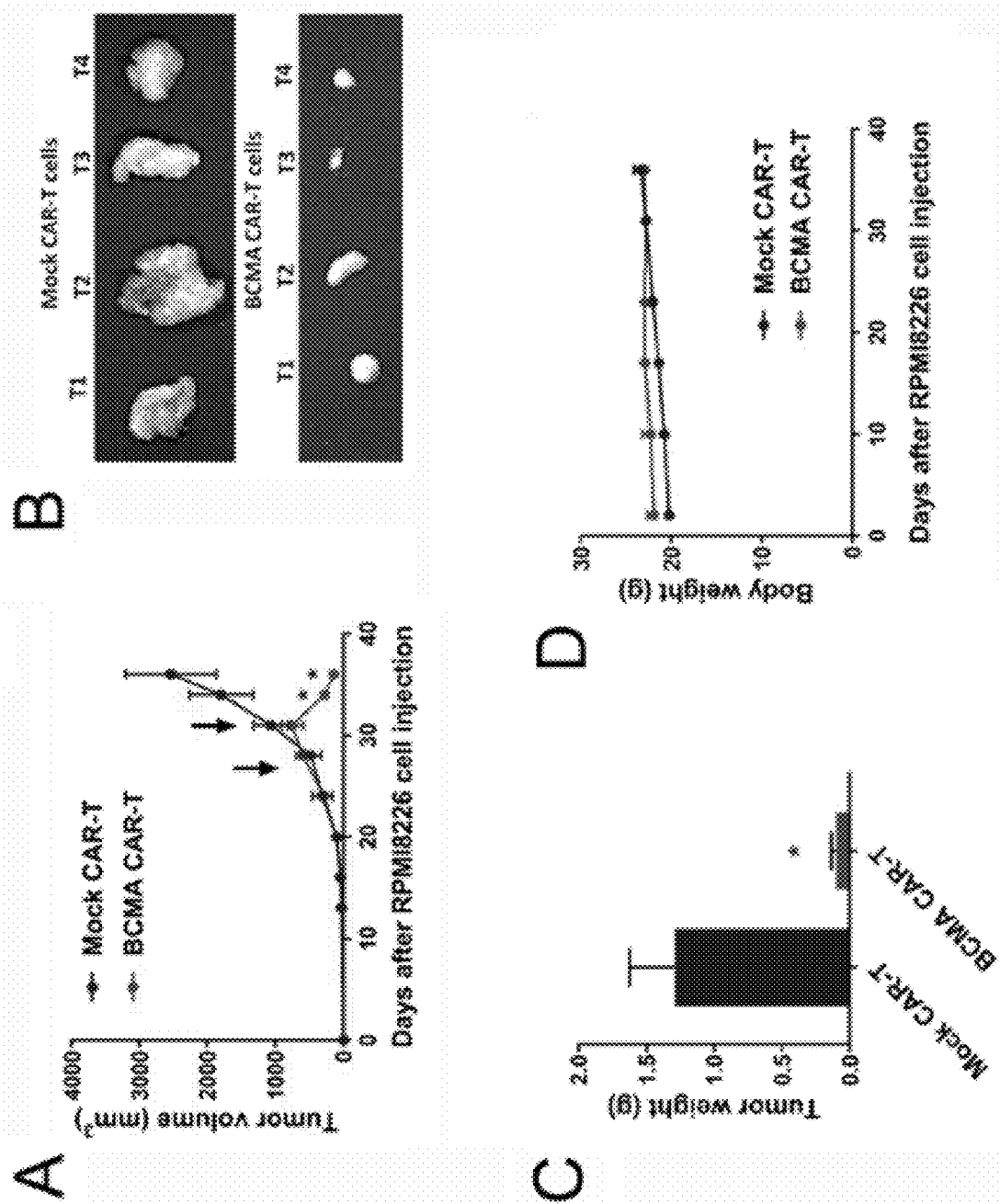
FIG. 13 shows that BCMA-CAR-T cells significantly decreased big RPMI8226 tumor xenograft tumor growth. Characterization of BCMA 4C8A CAR-T cells in a therapeutic mouse tumor model with 500 mm³ tumors. A: NSG mice were injected subcutaneously with RPMI8226 myeloma cells and tumor size was measured bi-weekly with calipers. On days 27 and 31 (arrows), the mice received BCMA CAR-T cells or mock CAR-T cells intravenously; *p<0.0001 for BCMA CAR-T cells vs mock CAR-T cells. B: The tumors were excised and photographed. C: The excised tumors were weighed; *p<0.05 for BCMA CAR-T cells vs mock CAR-T cells. D: The mice were weighed weekly during the study. BCMA-CAR-T cells do not decreased mouse body weight.

In the next experiment, multiple myeloma RPMI8226 cells were injected subcutaneously into NSG mice (1×10^7 cells/mice), and then BCMA-CAR-T cells were injected at day 27, 31 (1×10^7 CAR-T cells/mice) when tumor volumes reached about 500 mm$^3$ volume. BCMA-CAR-T cells significantly decreased RPMI8226 tumor growth in mice (FIG. 13). The tumor size, volume and weight were significantly decreased (FIG. 13). The mice treated with BCMA-CAR-T cells did not cause decreased mice body weight suggesting that CAR-T cells were not toxic to mice (FIG. 13D). In addition, immunohistochemistry analysis demonstrated that xenograft tumors contained human T cells confirming BCMA-CAR-T dependent mechanism. The xenograft tumors also had decreased Ki-67 staining and increased caspase-3 supporting decreased tumor growth.

The toxicology study was performed, and BCMA-CAR-T cells were not toxic to animals (data not shown).

REFERENCES

1. Maus, M. V., et al. (2013). Cancer Immunol Res 1, 26-31.
2. Maus, M. V., et al. (2014) Blood 123, 2625-2635
3. Ali, S. A., et al. (2016) Blood 128, 1688-1700.
4. Tai, Y. T., et al. (2015). Immunotherapy 7, 1187-99
5. Boeye, A. (1986). Methods Enzymol 121, 332-340.
6. Berahovich R, et al, (2018). Cancers, 11 Sep. 2010 PMID: 30208593

What is claimed is:

1. A monoclonal anti-human BCMA antibody comprising $V_H$ comprising the amino acid sequence of SEQ ID NO: 6 and $V_L$ comprising the amino acid sequence of SEQ ID NO: 7.

2. A single-chain variable fragment (scFv) comprising $V_H$ comprising the amino acid sequence of SEQ ID NO: 6, and $V_L$ comprising the amino acid sequence of SEQ ID NO: 7.

3. The scFv of claim 2, further comprises a linker in between $V_H$ and $V_L$.

4. The scFv of claim 3, which comprises the amino acid sequence of SEQ ID NO: 5.

5. A chimeric antigen receptor (CAR) comprising from N-terminus to C-terminus:

(i) the scFv of claim 2,
(ii) a transmembrane domain,
(iii) at least one co-stimulatory domains, and
(iv) an activating domain.

6. The CAR of claim 5, wherein the scFv comprises the amino acid sequence of SEQ ID NO: 5.

7. The CAR according to claim 5, wherein the co-stimulatory domain is CD28, 4-1BB, CD27, or GITR.

8. The CAR according to claim 5, wherein the co-stimulatory domain is CD28.

9. The CAR according to claim 5, wherein the activation domain is CD3 zeta.

* * * * *

SEQUENCE LISTING

<160> NUMBER OF SEQ ID NOS: 14

<210> SEQ ID NO 1
<211> LENGTH: 184
<212> TYPE: PRT
<213> ORGANISM: Homo sapiens

<400> SEQUENCE: 1

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140
```

```
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
            165                 170                 175

Ile Glu Lys Ser Ile Ser Ala Arg
            180
```

```
<210> SEQ ID NO 2
<211> LENGTH: 351
<212> TYPE: DNA
<213> ORGANISM: Mus musculus

<400> SEQUENCE: 2
gtccagctgc agcagtctgg acctgagctg gtaaagcctg ggcttcagt gaagatgtcc      60 tgcaaggctt ctggatacac attcactagc tatgttatgc actgggtgaa gcagaagcct     120
gggcagggcc ttgagtggat tggatatatt attccttaca atgatgctac taagtacaat     180
gagaagttca aggcaaggc cacactgact tcagacaaat cctccagcac agcctacatg      240
gagctcagca gcctgaccte tgaggactct gcggtctatt actgtgcacg ctataattac     300
gacgggtact tcgatgtctg gggcgcaggg accacggtca ccgtctcctc a              351

<210> SEQ ID NO 3
<211> LENGTH: 321
<212> TYPE: DNA
<213> ORGANISM: Mus musculus

<400> SEQUENCE: 3
gacattgtga tgactcagtc tccagccacc ctgtctgtga ctccaggaga tagagtctct     60
ctttcctgca gggccagcca gagtattagc gactacttac actggtatca acaaaaatca    120
catgagtctc caaggcttct catcaaatat gcttcccaat ccatctctgg gatcccctcc    180
aggttcagtg gcagtggatc agggtcagat ttcactctca gtatcaacag tgtggaacct    240
gaagatgttg gagtgtatta ctgtcaaaat ggtcacagct ttcctccgac gttcggtgga    300
ggcaccaagc tggaaatcaa a                                                321

<210> SEQ ID NO 4
<211> LENGTH: 45
<212> TYPE: DNA
<213> ORGANISM: Artificial Sequence
<220> FEATURE:
<223> OTHER INFORMATION: synthetic

<400> SEQUENCE: 4
ggtggcggtg gttctggtgg cggtggttct ggtggcggtg gttct                       45

<210> SEQ ID NO 5
<211> LENGTH: 239
<212> TYPE: PRT
<213> ORGANISM: Mus musculus

<400> SEQUENCE: 5

Val Gln Leu Gln Gln Ser Gly Pro Glu Leu Val Lys Pro Gly Ala Ser
1               5                   10                  15

Val Lys Met Ser Cys Lys Ala Ser Gly Tyr Thr Phe Thr Ser Tyr Val
                20                  25                  30

Met His Trp Val Lys Gln Lys Pro Gly Gln Gly Leu Glu Trp Ile Gly
            35                  40                  45

Tyr Ile Ile Pro Tyr Asn Asp Ala Thr Lys Tyr Asn Glu Lys Phe Lys
```

```
                 50                  55                  60
Gly Lys Ala Thr Leu Thr Ser Asp Lys Ser Ser Thr Ala Tyr Met
 65                  70                  75                  80

Glu Leu Ser Ser Leu Thr Ser Glu Asp Ser Ala Val Tyr Tyr Cys Ala
                         85                  90                  95

Arg Tyr Asn Tyr Asp Gly Tyr Phe Asp Val Trp Gly Ala Gly Thr Thr
                100                 105                 110

Val Thr Val Ser Ser Gly Gly Gly Ser Gly Gly Gly Ser Gly
            115                 120                 125

Gly Gly Gly Ser Asp Ile Val Met Thr Gln Ser Pro Ala Thr Leu Ser
130                 135                 140

Val Thr Pro Gly Asp Arg Val Ser Leu Ser Cys Arg Ala Ser Gln Ser
145                 150                 155                 160

Ile Ser Asp Tyr Leu His Trp Tyr Gln Gln Lys Ser His Glu Ser Pro
                165                 170                 175

Arg Leu Leu Ile Lys Tyr Ala Ser Gln Ser Ile Ser Gly Ile Pro Ser
                180                 185                 190

Arg Phe Ser Gly Ser Gly Ser Gly Ser Asp Phe Thr Leu Ser Ile Asn
                195                 200                 205

Ser Val Glu Pro Glu Asp Val Gly Val Tyr Tyr Cys Gln Asn Gly His
    210                 215                 220

Ser Phe Pro Pro Thr Phe Gly Gly Gly Thr Lys Leu Glu Ile Lys
225                 230                 235

<210> SEQ ID NO 6
<211> LENGTH: 117
<212> TYPE: PRT
<213> ORGANISM: Mus musculus

<400> SEQUENCE: 6

Val Gln Leu Gln Gln Ser Gly Pro Glu Leu Val Lys Pro Gly Ala Ser
  1               5                  10                  15

Val Lys Met Ser Cys Lys Ala Ser Gly Tyr Thr Phe Thr Ser Tyr Val
                 20                  25                  30

Met His Trp Val Lys Gln Lys Pro Gly Gln Gly Leu Glu Trp Ile Gly
             35                  40                  45

Tyr Ile Ile Pro Tyr Asn Asp Ala Thr Lys Tyr Asn Glu Lys Phe Lys
         50                  55                  60

Gly Lys Ala Thr Leu Thr Ser Asp Lys Ser Ser Thr Ala Tyr Met
 65                  70                  75                  80

Glu Leu Ser Ser Leu Thr Ser Glu Asp Ser Ala Val Tyr Tyr Cys Ala
                         85                  90                  95

Arg Tyr Asn Tyr Asp Gly Tyr Phe Asp Val Trp Gly Ala Gly Thr Thr
                100                 105                 110

Val Thr Val Ser Ser
            115

<210> SEQ ID NO 7
<211> LENGTH: 107
<212> TYPE: PRT
<213> ORGANISM: Mus musculus

<400> SEQUENCE: 7

Asp Ile Val Met Thr Gln Ser Pro Ala Thr Leu Ser Val Thr Pro Gly
  1               5                  10                  15

Asp Arg Val Ser Leu Ser Cys Arg Ala Ser Gln Ser Ile Ser Asp Tyr
```

```
                    20                  25                  30
Leu His Trp Tyr Gln Gln Lys Ser His Glu Ser Pro Arg Leu Leu Ile
                35                  40                  45

Lys Tyr Ala Ser Gln Ser Ile Ser Gly Ile Pro Ser Arg Phe Ser Gly
         50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Gly Gly Thr Lys Leu Glu Ile Lys
            100                 105
```

```
<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 63
<212> TYPE: DNA
<213> ORGANISM: Homo sapiens

<400> SEQUENCE: 9 atggcttac cagtgaccgc cttgctcctg ccgctggcct tgctgctcca cgccgccagg      60
ccg                                                                   63

<210> SEQ ID NO 10
<211> LENGTH: 717
<212> TYPE: DNA
<213> ORGANISM: Mus musculus

<400> SEQUENCE: 10
gtccagctgc agcagtctgg acctgagctg gtaaagcctg ggcttcagt gaagatgtcc      60 tgcaaggctt ctggatacac attcactagc tatgttatgc actgggtgaa gcagaagcct   120
gggcagggcc ttgagtggat tggatatatt ttccttaca atgatgctac taagtacaat    180
gagaagttca aggcaaggc cacactgact tcagacaaat cctccagcac agcctacatg    240
gagctcagca gcctgaccte tgaggactct gcggtctatt actgtgcacg ctataattac   300
gacgggtact cgatgtctg gggcgcaggg accacggtca ccgtctcctc aggtggcggt   360
ggttctggtg gcggtggttc tggtggcggt ggttctgaca ttgtgatgac tcagtctcca   420
gccaccctgt ctgtgactcc aggagataga gtctctcttt cctgcagggc cagccagagt   480
attagcgact acttacactg gtatcaacaa aaatcacatg agtctccaag gcttctcatc   540
aaatatgctt cccaatccat ctctgggatc ccctccaggt tcagtggcag tggatcaggg   600
tcagatttca ctctcagtat caacagtgtg gaacctgaag atgttggagt gtattactgt   660
caaaatggtc acagctttcc tccgacgttc ggtggaggca ccaagctgga aatcaaa      717

<210> SEQ ID NO 11
<211> LENGTH: 147
<212> TYPE: DNA
<213> ORGANISM: Homo sapiens
```

<400> SEQUENCE: 11

```
aagcccacca cgacgccagc gccgcgacca ccaacaccgg cgcccaccat cgcgtcgcag      60
cccctgtccc tgcgcccaga ggcgagccgg ccagcggcgg ggggcgcagt gcacacgagg     120
gggctggact tcgccagtga taagccc                                         147
```

<210> SEQ ID NO 12
<211> LENGTH: 204
<212> TYPE: DNA
<213> ORGANISM: Homo sapiens

<400> SEQUENCE: 12

```
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc cccgccgccc cgggcccacc cgcaagcatt accagcccta tgccccacca     180
cgcgacttcg cagcctatcg ctcc                                            204
```

<210> SEQ ID NO 13
<211> LENGTH: 345
<212> TYPE: DNA
<213> ORGANISM: Homo sapiens

<400> SEQUENCE: 13

```
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgcag agaaggaaga accctcagga aggcctgtac     180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg cccccctcgct aatag                    345
```

<210> SEQ ID NO 14
<211> LENGTH: 1488
<212> TYPE: DNA
<213> ORGANISM: Mus musculus

<400> SEQUENCE: 14

```
atggccttac cagtgaccgc cttgctcctg ccgctggcct tgctgctcca cgccgccagg      60
ccggctagcg tccagctgca gcagtctgga cctgagctgg taaagcctgg ggcttcagtg     120
aagatgtcct gcaaggcttc tggatacaca ttcactagct atgttatgca ctgggtgaag     180
cagaagcctg gcagggcct tgagtggatt ggatatatta ttccttacaa tgatgctact     240
aagtacaatg agaagttcaa aggcaaggcc acactgactt cagacaaatc ctccagcaca     300
gcctacatgg agctcagcag cctgacctct gaggactctg cggtctatta ctgtgcacgc     360
tataattacg acgggtactt cgatgtctgg ggcgcaggga ccacggtcac cgtctcctca     420
ggtggcggtg gttctggtgg cggtggttct ggtggcggtg gttctgacat tgtgatgact     480
cagtctccag ccaccctgtc tgtgactcca ggagatagag tctctctttc ctgcagggcc     540
agccagagta ttagcgacta cttacactgg tatcaacaaa aatcacatga gtctccaagg     600
cttctcatca aatatgcttc ccaatccatc tctgggatcc cctccaggtt cagtggcagt     660
ggatcagggt cagatttcac tctcagtatc aacagtgtgg aacctgaaga tgttggagtg     720
tattactgtc aaaatggtca cagctttcct ccgacgttcg gtggaggcac caagctggaa     780
```

```
atcaaactcg agaagcccac cacgacgcca gcgccgcgac caccaacacc ggcgcccacc      840
atcgcgtcgc agccctgtc cctgcgccca gaggcgagcc ggccagcggc gggggcgca        900 gtgcacacga gggggctgga cttcgccagt gataagccct tttgggtgct ggtggtggtt     960
ggtggagtcc tggcttgcta tagcttgcta gtaacagtgg cctttattat tttctgggtg     1020
aggagtaaga ggagcaggct cctgcacagt gactacatga acatgactcc ccgccgcccc     1080
gggcccaccc gcaagcatta ccagccctat gccccaccac gcgacttcgc agcctatcgc     1140
tccagagtga agttcagcag gagcgcagac gcccccgcgt accagcaggg ccagaaccag     1200
ctctataacg agctcaatct aggacgaaga gaggagtacg atgttttgga caagagacgt     1260
ggccgggacc ctgagatggg gggaaagccg cagagaagga agaaccctca ggaaggcctg     1320
tacaatgaac tgcagaaaga taagatggcg gaggcctaca gtgagattgg gatgaaaggc     1380
gagcgccgga ggggcaaggg gcacgatggc ctttaccagg gtctcagtac agccaccaag    1440
gacacctacg acgcccttca catgcaggcc ctgccccctc gctaatag                  1488
```